United States Patent [19]

Fernandez et al.

[11] Patent Number: 4,923,819
[45] Date of Patent: May 8, 1990

[54] TIME-RESOLVED FLUORESCENCE IMMUNOASSAY

[75] Inventors: Salvador M. Fernandez, Hartford; Hann-Ping Wang, Glastonbury; Yong-Sheng Chao, Glaston; Ernest F. Guignon, Canton, all of Conn.

[73] Assignee: Chimerix Corporation, Glastonbury, Conn.

[21] Appl. No.: 31,408

[22] Filed: Mar. 27, 1987

[51] Int. Cl.$^5$ ................ G01N 33/533; G01N 33/543; G01N 33/546; G01N 33/536

[52] U.S. Cl. .................... 436/518; 436/534; 436/536; 436/546; 436/805; 436/815; 436/818; 435/5; 435/7

[58] Field of Search ............ 436/536, 546, 800, 805, 436/518, 533, 534, 505, 815, 817, 818, 820

[56] References Cited

U.S. PATENT DOCUMENTS

| | | | |
|---|---|---|---|
| 4,058,732 | 11/1977 | Wieder | 250/461 B |
| 4,098,876 | 7/1978 | Piasio et al. | 436/500 |
| 4,146,602 | 3/1979 | Gutcho et al. | 424/1.1 |
| 4,231,750 | 11/1980 | Dowben et al. | 23/230 B |
| 4,235,864 | 11/1980 | Kaul et al. | 436/542 |
| 4,368,047 | 1/1983 | Andrade et al. | 435/4 |
| 4,374,120 | 2/1983 | Soini et al. | 436/546 |
| 4,385,126 | 5/1983 | Chen et al. | 436/518 |
| 4,582,809 | 4/1986 | Block et al. | 436/527 |
| 4,587,223 | 5/1986 | Soini et al. | 436/536 |
| 4,672,028 | 6/1987 | Olson | 435/5 |
| 4,690,890 | 9/1987 | Loor et al. | 435/7 |
| 4,713,348 | 12/1987 | Ullman | 436/501 |
| 4,772,563 | 9/1988 | Evangelista et al. | 436/805 |

OTHER PUBLICATIONS

"Enzyme-Immunoassay", E. T. Maggio, editor, 1980, p. 61 and p. 171.

"Time-Resolved Fluorescence Spectroscopy", Salvador M. Fernandez, *Fast Methods in Physical Biochemistry and Cell Biology*, Elsevier Science Publishers 1983, pp. 221–280.

*Primary Examiner*—Esther M. Kepplinger
*Attorney, Agent, or Firm*—Hamilton, Brook, Smith & Reynolds

[57] ABSTRACT

Fluorescence immunoassay for determining single or multiple analytes based upon a single measurement of fluorescence are described.

12 Claims, 3 Drawing Sheets

TIME-RESOLVED FLUORESCENCE IMMUNOASSAY

BACKGROUND

Since immunoassay was first described by Berson and Yalow in the late 1960's, a number of immunoassays with different assay formats (e.g. competitive vs. noncompetitive), different separation techniques (e.g., secondary antibody separation vs. solid phase separation), and different labels (e.g., isotopic vs. non-isotopic), have been developed for the detection of a wide spectrum of substances including molecules as small as digoxin and as large as a virus. Until recently, all these assays employed only one signal-generating label at a time which resulted in the limitation of detecting one substance (analyte) in one measurement.

The use of two radioisotopes, i.e., iodine 125 and cobalt 57, in a radioimmunoassay for detecting two analytes simultaneously in a single measurement has been demonstrated in a Vitamin B 12/Folate test (U.S. Pat. No. 4,146,602, Gutcho et al.) a TSH/ Free T4 test (Simultrac TM FT4/TSH, Becton Dickinson Immunodiagnostics), and the LH/FSH test (ComboStat TM LH/FSH, Micromedic Systems, ICN). In these assays, the discrimination between radioisotopes in the measurement is based on differences in their energy spectra.

The use of two fluorophores, e.g., fluorescein and rhodamine, in a qualitative immunoassay for detecting two substances simultaneously in a single sample but not in a single measurement has been demonstrated in the cell sorting techniques (FACS TM Cell Sorting System, Becton Dickinson). Recently, the use of two fluorophores, i.e. fluorescein and phycoerythrin, in a quantitative immunoassay for detecting human IgG and IgM in a single sample but not in a single measurement, was reported (R. Houghton, Abstract, *Clin. Chem.* Vol. 32, p. 1067, 0 1986). In these fluorescence-based immunoassays, the resolution of the fluorophores in the measurement is based on the differences in their excitation and emission spectra.

A method of time-resolved immunoassay is described in U.S. patents 4,058,732 and 4,374,120. In this method a fluorescent probe is employed that has a fluorescence decay (lifetime) that substantially exceeds the duration of the exciting pulse and the duration of the background non-specific fluorescence. A time-gating is used to reduce the background fluorescence, i.e., the measurement of the fluorescence is delayed until a certain time has elapsed from the moment of excitation. The delay time is sufficiently long for the background fluorescence to have ceased. When the fluorescence signal is measured (after the delay) the measurement is an integrated measurement, i.e. all the light arriving at the detector during the measuring period is measured without regard to the time of arrival. The purpose of this delayed measurement is to ensure that only one fluorescence signal reaches the detector during measurement. used to selectively detect and quantify the different analytes.

The fluorescence immunochemical assays of this invention can be performed in the heterogeneous or homogeneous, competitive or noncompetitive modes. In each assay mode, a fluorescently labeled analyte or antibody is employed and the fluorescence emitted is proportional (either directly or inversely) to the amount of analyte. The amount of fluorescence is determined by the amplitude of the fluorescence decay curve for the fluorescent species. This amplitude parameter is directly proportional to the amount of fluorescent species and accordingly to the analyte.

In general spectroscopic measurement of fluorescence is accomplished by:

a. exciting the fluorophore with a pulse of light;
b. detecting and storing an image of the excitation pulse and an image of all the fluorescence (the fluorescent transient) induced by the excitation pulse;
c. digitizing the image;
e. calculating the true fluorescent transient from the digitized data;
f. determining the amplitude of the fluorescent transient as an indication of the amount of fluorescent species.

In assays for multiple analytes where two or more fluorescent species contribute to the overall fluorescence, the fluorescent transient for each component is determined based upon the known fluorescence lifetime of each fluorescent species.

According to the method, substantially all of the fluorescence emitted by the fluorescent species reaching the detector as a function of time from the instant of excitation is measured. As a consequence, the signal being detected is a superimposition of several component signals (for example, background and one analyte specific signal; or signals from different labeled analytes in the case of a multiple analyte assay, etc.). As mentioned, the individual contributions to the overall fluorescence reaching the detector are distinguished based on the different fluorescence decay rates (lifetimes) of signal components. In order to quantitate the magnitude of each contribution, the detected signal data is processed to obtain the amplitude of each component. The amplitude of each component signal is proportional to the concentration of the fluorescent species.

The advantages of the time-resolved fluorescence immunoassay of this invention include no handling of hazardous radioactive material, and the ability to determine more than one analyte in a single sample in one measurement which is cost effective. Furthermore, the present invention minimizes the problem of background noise which is commonplace in the fluorescence immunoassay (especially in the homogenous mode). This is because the decay lifetime of background fluorescence is usually significantly shorter than the decay lifetime of the fluorescence of fluorophores used in the immunoassay.

SUMMARY OF THE INVENTION

This invention pertains to a fluorescence immunoassay for the detection of one, two or more analytes in a single sample which requires only a single measurement of the signal generated by the fluorescently labeled species. In assays for multiple analytes, different fluorescent probes having distinct fluorescence lifetimes are

DETAILED DESCRIPTION OF INVENTION

Immunoassay Formats

Figure 1:
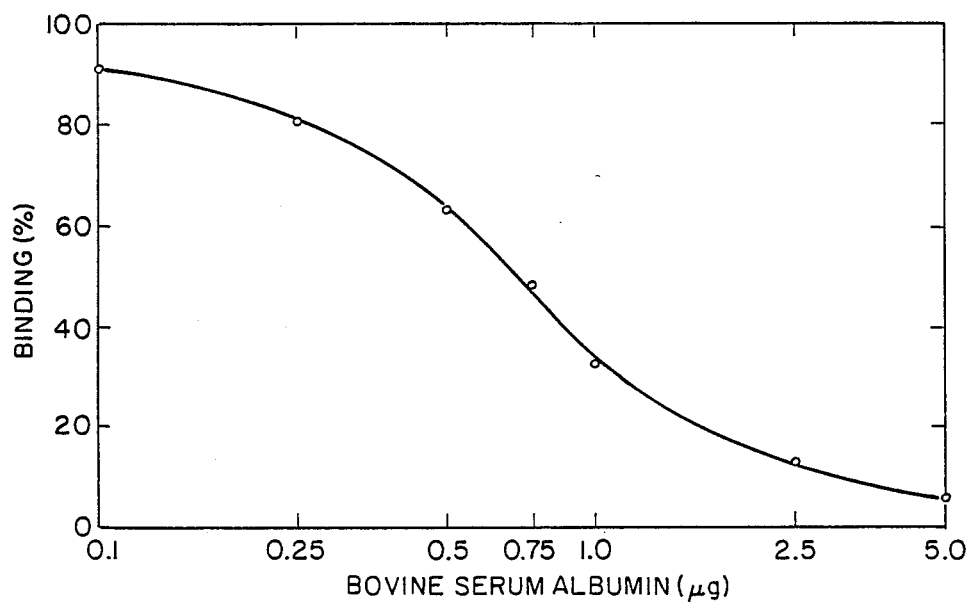
FIG. 1 shows an inhibition curve for a competitive binding assay for bovine serum albumin (BSA) where the amount of fluorescently labeled BSA bound is determined by measuring fluorescece intensity.

The fluorescence immunoassays of this invention can be performed in competitive or noncompetitive format; and they may be performed in the heterogenous or homogenous mode.

In a heterogeneous assay, the bound analyte is separated from unbound (free) analyte and the amount of bound or free is measured. Heterogeneous assays based upon the use of a solid phase to effectuate separation of bound from free analyte are described in detail below. In an homogeneous mode, no separation step is needed. The bound form of analyte (or antibody) and the free form are distinguished by a detectable change in the fluorescence lifetime of the labeled species which is induced by binding.

The competitive format is based upon the ability of unlabeled analyte to compete with fluorescently labeled analyte and to inhibit the binding of labeled analyte to a limited amount of antibody against the analyte. As a result of the competitive inhibition the proportion of bound labeled analyte decreases as the concentration of unlabeled analyte increases. The concentration of unlabeled analyte in the sample is determined by referring to a standard inhibition curve.

In a competitive assay for two or more analytes, antibody for each analyte to be determined is incubated with the sample to be tested and with fixed amounts of the analytes, each analyte being labeled with a distinct fluorophore. As a conjugate species, each labeled analyte has a different, known fluorescence lifetime (see below for a detailed discussion for the properties of the fluorophores and fluorophore conjugates). Based on this difference, the contribution of each fluorophore to the total fluorescence emitted upon excitation can be distinguished. The amount of each labeled analyte bound by antibody is determined by the amplitude of the fluorescence decay curve for each analyte. The amplitude of the fluorescence decay curve of each component is directly proportional to the amount of conjugate, which is inversely proportional to the amount of unlabeled analyte in the test sample Non-competitive immunoassays are based on the reaction of analyte with an excess amount of antibody (capture antibody). The complexed analyte is then measured and this amount of complexed analyte is directly proportional to the amount of analyte in a sample. The immunocomplex between the capture antibody and analyte is detected with a fluorophorelabeled antibody conjugate against either component of the complex (i.e. the analyte or the capture antibody). The antibody conjugate is reacted with the complex of capture antibody-analyte and the amount of fluorescent label associated with the complex is directly proportional to the amount of analyte in the sample. The amount of fluorescence associated with the complex is determined by measuring the amplitude of the fluorescence decay curve for the conjugate.

In an immunometric assay for multiple analytes a mixture of capture antibodies containing antibody specific for each analyte is employed. Fluorescently labeled antibody conjugates specific for each capture antibody-analyte complex—each conjugate having a different fluorescence lifetime—are used to determine the amount of analyte complexed with its respective capture antibody. The fluorescent conjugate can comprise, for example, a fluorophore linked to a second antibody specific for an analyte. The fluorophore for each analyte-specific antibody has fluorescence characteristics which results in conjugates having different fluorescence lifetimes.

The preferred assay format for simultaneous determination of two or more analytes is a solid phase immunometric assay. Especially preferred is the "sandwich" type assay. The preferred mode is the forward mode but reverse and simultaneous modes may also be used. In assays of this format, an immunoadsorbent is provided which comprises a solid phase to which is affixed capture antibody specific for each of the analytes to be determined. The immunoadsorbent is incubated with the sample to be tested under conditions and for a period of time sufficient for analytes in the sample to complex with their respective capture antibodies on the solid phase. After the incubation, the immunoadsorbent and the sample are separated. Normally, the solid phase is then washed to remove unbound and/or nonspecifically adsorbed substances.

The amount of each analyte bound to the immunoadsorbent is determined by means of fluorescent conjugates specific for each analyte which have distinct fluorescence lifetimes. As explained, the fluorescence lifetime provides a means of distinguishing between the conjugates and thus, determining the amount of each analyte.

In one embodiment of the assay, a solution of fluorescent antibody conjugates is incubated with the immunoadsorbent under conditions and for a period of time sufficient for the conjugates to complex analytes associated with the solid phase. After the incubation period, the immunoadsorbent and the solution are separated and the fluorescence associated with the solid phase is analyzed by time resolved spectroscopy as described herein. The fluorescence associated with solid phase may be analyzed while the fluorescence conjugate is affixed to the solid phase or the conjugate may be removed from the solid phase (e.g. by eluting the conjugate from the solid phase under alkaline conditions) and analyzed in suspension or in solution.

In another embodiment, the amount of analyte can be analyzed by employing a second antibody to bind the analyte associated with the immunoadsorbent and then employing a fluorescent antibody conjugate against the second antibody to determine the amount of analyte. In assays for multiple analytes, the second antibodies against each analyte are antigenically distinguishable. The conjugates comprise fluorescently labeled antibodies against the second antibodies. Each conjugate has a different fluorescence lifetime, which provides the basis for distinguishing the contributoion of each to the overall fluorescence signal generated upon excitation.

The second antibodies used in assays of this type can be derived from different animal species. In an assay for two analytes, for example, the second antibody against one analyte can be a murine antibody and the conjugate can be a labeled anti-murine antibody. The second antibody against a second analyte can be a rabbit antibody and the fluorescent conjugate can be a fluorescently labeled anti-rabbit antibody.

The antibodies used in the assays of this invention can be monoclonal antibodies, polyclonal antibodies, or both. In the embodiment where a second antibody is employed, the preferred kinds of antibody are as follows: the capture (solid phase) antibody is a monoclonal antibody, the second antibody against the analyte is polyclonal and the fluorescent conjugate contains a polyclonal antibody against the second antibody. The use of a polyclonal antibody as second antibody and as the antibody component of the conjugates results in an amplification of fluorescence signal because of the multi-epitopic binding of polyclonal antibodies.

Fluorescent Conjugates

The fluorescent conjugates comprise conjugates of a fluorophore and either an analyte or antibody (depending on the assay format). The conjugates can be prepared by standard techniques for conjugation of fluorophores to proteinaceous and nonproteinaceous analytes and/or to antibodies. For example, fluorophores can be conjugated to proteins via functional groups such as amine, carboxyl or sulfhydryl groups. Fluorophores can also be linked through various carbohydrate moieties to carbohydrates or analytes which contain carbohydrate moieties such as glycoproteins. A preferred technique for conjugation is the isothiocyanate technique. The isothiocyanate group is very reactive to primary amino groups of proteins. Preferred fluorophores have appropriate groups such for linkage to protein either directly or via a linker.

Before use in the assays the conjugates are characterized as to spectral characteristics including optimal excitation and emission wavelength and fluorescence lifetime. All of these properties of the conjugate can be determined by standard techniques. The fluorescence lifetime of the conjugate may vary dependent upon the ratio of fluorophore to analyte/antibody in the conjugate. For proteins this ratio is referred to as the dye/protein (D/P) ratio. In general, conjugates having a high D/P ratio are preferred because this enhances the sensitivity of the assay. However, D/P ratios which are too high may lead to self-quenching or loss of immunoreactivity of a labeled antigen or antibody. The optimal D/P ratio for any specific conjugate can be determined empirically.

Fluorophores

For the purposes of the invention a fluorophore can be a substance which itself fluoresces or can be made to fluoresce or it can be a fluorescent analogue of an analyte.

In principle, any fluorophore can be used in the assays of this invention. Preferred fluorophores, however, have the following characteristics:
  a. A fluorescence lifetime of greater than about 15 nsec;
  b. An excitation wavelength of greater than about 350 nm;
  c. A Stoke's shift (a shift to lower wave-length of the emission relative to absorption) of greater than about 20 nm;
  d. for homogeneous asays, fluorescence lifetime should vary with binding status; and
  e. The absorptivity and quantum yield of the fluorophore should be high.

The longer lifetime is advantageous because it is easier to measure and more easily distinguishable from the Raleigh scattering (background). Excitation wavelengths greater than 350 nm reduce background interference because most fluorescent substances responsible for background fluorescence in biological samples are excited below 350 nm. A greater Stoke's shift also allows for less background interference.

The fluorophore should have a functional group available for conjugation either directly or indirectly to analyte/antibody. An additional criterion in selecting the fluorophore is the stability of the fluorophore: it should not be photophysically unstable, and it should be relatively insensitive to the assay conditions, e.g., pH, polarity, temperature and ionic strength.

Preferably (though not necessarily), fluorophores for use in heterogenous assays are relatively insensitive to binding status. In contrast, fluorophores for use in homogeneous assay must be sensitive to binding status, i.e., the fluorescence lifetime must be alterable by binding so that bound and free forms can be distinguished.

In choosing two or more fluorophores for use in assays for multiple analytes, the following criteria pertain:
  a. Ideally, the fluorophores should have substantial overlap of absorption bands so that they may be efficiently excited at a single wavelength.
  b. The emission wavelengths should have substantial overlap of emission bands so that the fluorescence contribution of each probe can be effectively monitored at a single wavelength.
  c. The difference in fluorescence lifetime between fluorophores should be at least about 5 nsec.

Examples of fluorophores useful in the invention are naphthalene derivatives (e.g. dansyl chloride), anthracene derivatives (e.g. N-hydroxysuccinimide ester of anthracene propionate), pyrene derivatives (e.g. N-hydroxysuccinimide ester of pyrene butyrate), fluorescein derivatives (e.g. fluorescein isothiocyanate) and rhodamine derivative (e.g. rhodamine isothiocyanate).

Other Parameters of Assays

For each incubation step in the various formats of the assays, the time and conditions of incubation are selected to ensure maximal binding of analyte to the immobilized antibody (the immunoadsorbent) and to the fluorescent conjugate. Optimal conditions of pH, temperature, incubation time, and ionic strength for each incubation can be determined empirically.

In the heterogeneous solid phase assay of this invention, the immunoadsorbent is separated from incubation mixtures containing the liquid test sample or the fluorescent probe. Separation can be accomplished by any conventional separation technique such as sedimentation or centrifugation. Preferably, (though not necessarily), the immunoadsorbent is washed prior to contacting it, when required, with a second incubation medium and prior to measuring the amount of fluorescent conjugate associated with the immunoadsorbent. The washing removes nonspecific interfering substances or excess labeled antibody which may affect the accuracy and sensitivity of the assay.

The immunoassays of this invention are used to detect and quantify analytes in a liquid sample or histological specimen. Liquid samples include essentially all biological fluids such as blood, or components of blood such as plasma or serum and urine, lymph, etc. Also, the liquid sample may be a sample of a liquid medium in which lymphocytes or other mammalian cells have been cultured. They may also be extracts or supernatants of microbial cultures or environmental samples such as sewage effluents, etc. Histological specimens include tissue slices or cell samples.

Many types of solid phases can be employed in the preferred assays of this invention. These include beads formed from glass, polystyrene, polypropylene, dextran, and other materials; the microwells of a microwell plate or tubes formed from or coated with such materials, etc. The antibody can be either covalently or non-covalently bound to the solid-phase by techniques such as covalent bonding via an amide or ester linkage, biotin-avidin bridges or adsorption. Those skilled in the art will know many other suitable solid-phases and methods for immobilizing antibodies thereon, or will be able to ascertain such using no more than routine experimentation.

To determine the amount of analyte in a liquid sample, either the amount of fluorescent conjugate associated with the immunoadsorbent or the amount of unbound conjugate (i.e. that which remains in soluble form), is measured. Generally, it is preferable to measure the conjugate bound to the immunoadsorbent because at very low concentrations of antigen, only small amounts of labeled antibody bind the immunoadsorbent. Thus, for accuracy the fluorescent label associated with the immunoadsorbent should be measured.

The reagents for performance of the assays in their various formats may be assembled in assay kits. For instance, a kit for performing a solid phase immunometric assay for multiple analytes may comprise:
(a) a solid phase immunoadsorbent containing capture antibody specific for each analyte to be measured; and
(b) fluorescent conjugates comprising antibody specific for each analyte and a fluorophore, each conjugate having a different fluorescence lifetime.

A kit for performing a solid phase immunometric assay for multiple analytes where a secondary antibody is employed can comprise:
(a) a solid phase immunoadsorbent containing capture antibody specific for each analyte to be measured;
(b) second antibodies specific for each analyte, each second antibody being antigenically distinct; and
(c) fluorescent conjugates comprising antibody against the second antibody and a fluorophore, each conjugate having a distinct fluorescence lifetime.

As mentioned, in a preferred configuration, the capture antibody can be monoclonal and the second antibody and antibody conjugate can be polyclonal.

Analytes

Virtually all types of analytes can be determined by the method of the invention. These include hormones, vitamins, therapeutic drugs, drugs of abuse, tumor markers, neonatal markers, microbes, viruses and antibodies. Examples of some specific protein hormones include thyroid stimulating hormone (TSH), Luteinizing hormone (LH), Follicle stimulating hormone (FSH), growth hormone (GH), human chorionic gonadotropin (hCG) and adrenocorticotrophic hormone (ACTH). Steroid hormones include androgens, progestins, estrogens, corticosteroids and aldosterone. Therapeutic drugs include theophylline, digoxin, dilantin and phenobarbital. Viruses such as hepatitis virus, human immunodeficiency virus and herpes viruses, viral components, or antibodies against these viruses (as an indication of infection) can also be detected.

In the design of assays for two or more analytes, clinically related analytes can be combined. Examples of such combinations are TSH/Free $T_4$, LH/FSH, Vitamin B12/Folate, B-HCG/AFP, CEA/PAP, CK/CK-MB, $LDH_1/LDH_2$, HIV/HBAgs, HBAgs/HBAgc, Herpes/Chlamydia and $TSH/T_4/TBG$.

Fluorescence Spectroscopy

The time-resolved fluorescence spectroscopy employed in the method of this invention and instruments for performing the method are described in detail in U.S. Patent Application Ser. No. 031,288, entitled "Method and Apparatus for Improved Time Resolved Fluorescence Spectroscopy", Chao, Y-S. et al., filed concurrently herewith, the teachings of which are incorporated herein by reference.

According to the method of this invention, all the fluorescence reaching the detector as a function of time from the instant of excitation is measured. Thus, the detected signal is a superposition of several signals (for example, background and one analyte-specific signal; or signals from different labeled analytes in the case of a multiple analyte assay, etc.). The individual contributions to the overall fluorescence reaching the detector are distinguished based on the different fluorescence decay rate (lifetime) of signal. The amplitude of a component of the signal is proportional to the specie responsible for the signal component.

In the preferred mode, the amplitude of the fluorescence signal is determined by:
(a) exciting the fluorescent species with a single pulse of light energy to induce fluorescence;
(b) separately detecting in a detector and generating:
(i) an electrical signal corresponding to the fluorescence transient waveform F(t) induced by the single pulse, as distorted by said detector and the pulse, and
(ii) an electrical signal corresponding to the waveform E(t) of the single pulse, as distorted by the impulse response of the detector,
(c) separately displaying an image of the waveforms F(t) and E(t);
(d) digitizing a predetermined number of data points on each such image, as digital numbers representing points on the waveforms;
(e) storing the numbers in memory as data points of T(t) and F(t); and
(f) calculating the true impulse response fluorescence waveform F(t) from the stored data point numbers by convoluting E(t) with a predetermined trial function $F(t)_{calc}$ having adjustable parameters and comparing the data points of the convoluted $F(t)_{calc}$ with data points corresponding to F(t) data points.

Where a single fluorescent species is employed (e.g. in assays for a single analyte), the trial function curve is an exponential curve in the form of $A\exp(-t/T)$ wherein the parameter A is the amplitude and T is the fluorescence decay lifetime. Where a plural number of fluorescent species are employed (e.g. assays for multiple analytes) the trial function is the sum of a plural number, ith, of exponential curves $A_1\exp(-t/T_1)+A_2\exp(-t/T_2) \cdots A_{ith}\exp(-t/T_{ith})$ T, the fluorescence lifetime, is known in advance (as it is a property of the fluorescent conjugate (or fluorescent analogue) employed in the assay) and the parameter A is proportional to the concentration of the fluorescent specie. With two fluorescent species, the lifetimes of which are known in advance, the amplitude parameter is proportional to the concentration of each fluorescent species. The absolute concentration of the fluorescent species is determined by comparing the calculated amplitude parameter with a standard curve which has been obtained in advance which provides the relationship between concentration and amplitude of the fluorescence transient waveform.

The invention is illustrated further by the following exemplification.

EXEMPLIFICATION

Preparation of dansylated BSA (bovine serum albumin)

BSA (6.9 mg) was dissolved in 1.0 ml of sodium borate buffer (0.1 M, pH 9.0) and the resulting solution was stirred. To this solution, dansyl chloride (2.8 mg) in 50 ul dimethyl formamide (DMF) was added dropwise over a period of 3 minutes at room temperature. The resulting solution was stirred for an additional 18 hours at room temperature. The reaction mixture was centrifuged to remove any particulate, and the resulting supernatant was applied onto a Sephadex G-25 gel filtration column (1.6 cm×45 cm) which was previously equilibrated in phosphate buffered saline (PBS; 10 mM sodium phosphate buffer, pH 7.4, 0.15 M NaCl) and the same buffer was used for elution. The protein elution profile was monitored by a 280 nm UV detector, the protein conjugate fraction was collected (the conjugate was in the first eluted peak) and the dansyl-BSA conjugate (stock solution; 564 ug/ml) was stored at 4° C. until use.

Preparation of human serum albumin (HSA) pyrene butyrate conjugate

HSA (6.9 mg) was dissolved in 1 ml of 0.1 M sodium borate buffer, pH 9.0, and the solution was kept stirred at room temperature. To this solution, pyrene butyrate succinimide ester (3.2 mg) in 50 ul of DMF was added dropwise over a period of 3 minutes. The resulting solution was stirred for an additional 18 hours at room temperature, and the reaction mixture was centrifuged to remove any particulate. The supernatant was applied onto a Sephadex G-25 gel filtration column chromatography (same column size and elution buffer as above) to remove any unconjugated pyrene butyrate ester. The protein elution profile was monitored using a 280 nm UV detector and the protein-pyrene butyrate conjugate (stock solution 290 ug/ml) was collected and stored at 4° C. until use.

Characterization of dansyl-BSA and pyrene butyrate-HSA conjugates.

Protein concentration of the conjugates was determined by the Lowry technique. The concentrations of the fluorophores was determined by spectrophotometric methods (See Chen, R., *Anal. Biochem.* Vol. 25, pp 412–416, 1968 and Rawitch, A.B., et al., *J. Biol. Chem.* Vol. 244, pp 6543–6547, 1969), and the dye/protein (D/P) ratios were calculated. The D/P ratios were between 3.5 and 52.5 for the dansyl-BSA conjugate and between 3 and 71 for the pyrene butyrate-HSA conjugate. The fluorescence excitation and emission spectra of the conjugates were measured. The excitation maximum was at 347 nm and the emission maximum was at 515 nm for the dansyl-BSA conjugate regardless of the D/P ratios. For the pyrene butyrate-HSA conjugate, the excitation maximum was at 347 nm with a secondary peak at 337 nm, and the emission maximum was at 376 nm or at 465 nm with a secondary peak at 395 nm depending on the D/P ratios. The lifetime of the fluorescence decay of the conjugates was also measured. The lifetimes were between 15 ns and 20 ns for the dansyl-BSA conjugates and between 70 and 100 ns for the pyrene butyrate-HSA conjugates depending on the D/P ratios of the conjugates. The larger the D/P ratio was, the shorter was the life time. Dansyl-BSA conjugates chosen had a D/P of 48 and a lifetime of 16 ns; pyrene butyrate-HSA conjugate had a D/P of 41 and a lifetime of 84 ns. Antibody binding activity was measured on Ouchterlony radial immunodiffusion plate (0.6% agarose in PBS containing 0.01% sodium azide) in which the conjugate was loaded into one well and its corresponding antibody into another well. The plate was incubated at room temperature for 4 hours. Fluorescence immuno-precipitin bands were observed under a short wave UV hand lamp. The anti-BSA dansyl-BSA immunoprecipitin band was bluish and the anti-HSA pyrene butyrate HSA-immunoprecipitin band wa greenish.

IMMUNOASSAY PROCEDURES

Single analyte fluorescence immunoassay

Figure 2:
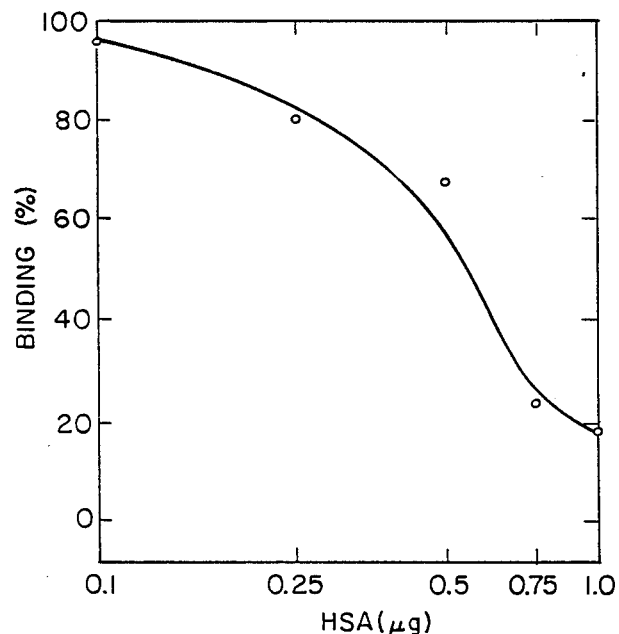
FIG. 2 shows an inhibition curve for a competitive binding assay for human serum albumin (HSA) where the amount of fluorescently labeled HSA bound is determined by measuring fluorescence intensity

Dansyl-BSA conjugate (100 ul of a forty-fold dilution of the stock solution) or pyrene butyrate-HSA conjugate (100 ul of four hundred-fold dilution of the stock solution) was incubated with 100 ul of its respective antibody (produced in rabbit) at (1/125 dilution anti-HSA; 1/75 dilution anti-BSA, Cooper Biomedical Co. Pa.) in the absence of unlabeled BSA or HSA, or in the presence of varying amount of unlabeled BSA (0.1, 0.25, 0.5, 0.75, 1.0, 2.5, and 5.0 ug in 100 ul) or unlabeled HSA (0.1, 0.25, 0.5, 0.75, and 1.0 ug in 100 ul), respectively. To the reaction mixture, 100 ul normal rabbit serum (4% in PBS) was added. The incubation was performed in PBS containing 0.1% gelatin and 0.1% sodium azide at 37 C for 60 minutes in a shaking water bath. 100 ul each of goat anti-rabbit IgG (20% in PBS) and polyethylene glycol (12.5% in water) were added and incubated at 37° C. for an additional 30 minutes in a shaking water bath. At the end of the incubation, PBS (2 ml) containing 0.1% sodium azide was added, then the incubation mixture was centrifuged for ten minutes and the pellet collected. To the pellet, 200 ul each of 0.1N NaOH, 0.1 N HCl and PBS were added in sequence to resuspend and stabilize the conjugate. For conventional fluorescence immunoassay, the fluorescence intensity of the suspension was measured by spectrofluorometer (SLM 8000 C.) and the dose response curve was constructed by plotting the concentration of the unlabeled BSA or unlabeled HSA against the fluorescence intensity (FIGS. 1 and 2).

Figure 3:
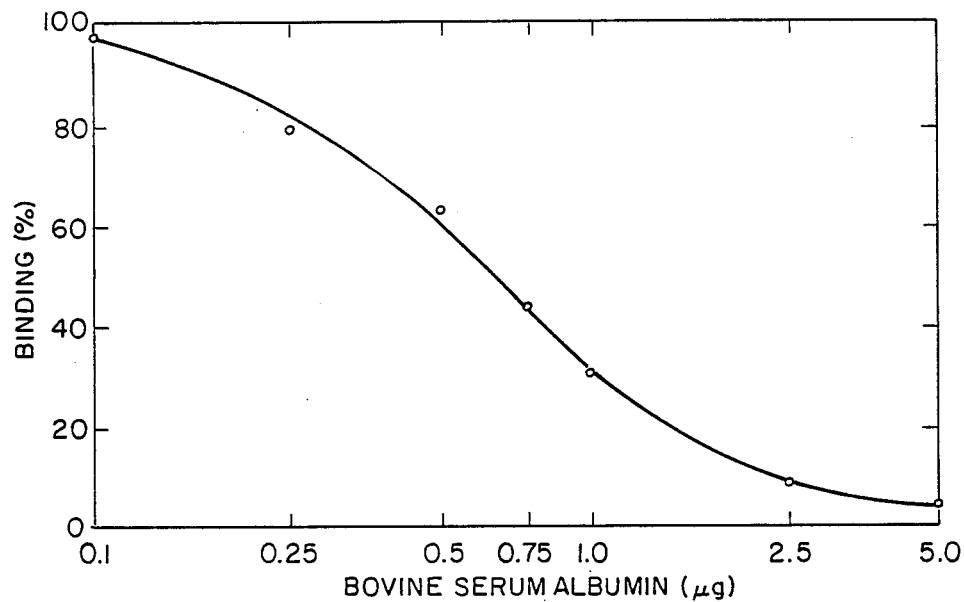
FIG. 3 shows an inhibition curve for a competitive binding assay for BSA where the amount of fluorescently labeled BSA bound is determined by the amplitude of the flurescence decay curve.
Figure 4:
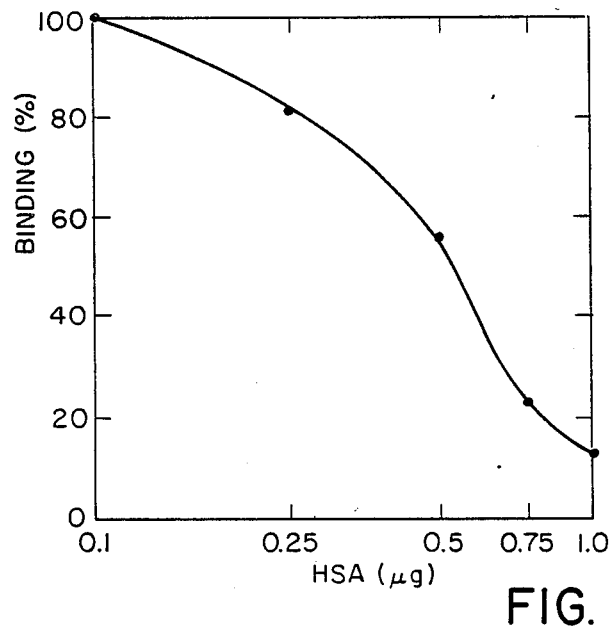
FIG. 4 shows an inhibition curve for a competitive binding assay for HSA where the amount of fluorescently labeled HSA bound is determined by the amplitude of the fluorescence decay curve.

For time-resolved fluorescence immunoassay, deconvolution analysis of the fluorescence decay curve of the suspension was performed and the dose response curve was constructed by plotting the concentration of unlabeled BSA or unlabeled HSA against the amplitude from the convolution curve (FIGS. 3 and 4).

Multi-analyte time-resolved fluorescence immunoassay

Figure 5:
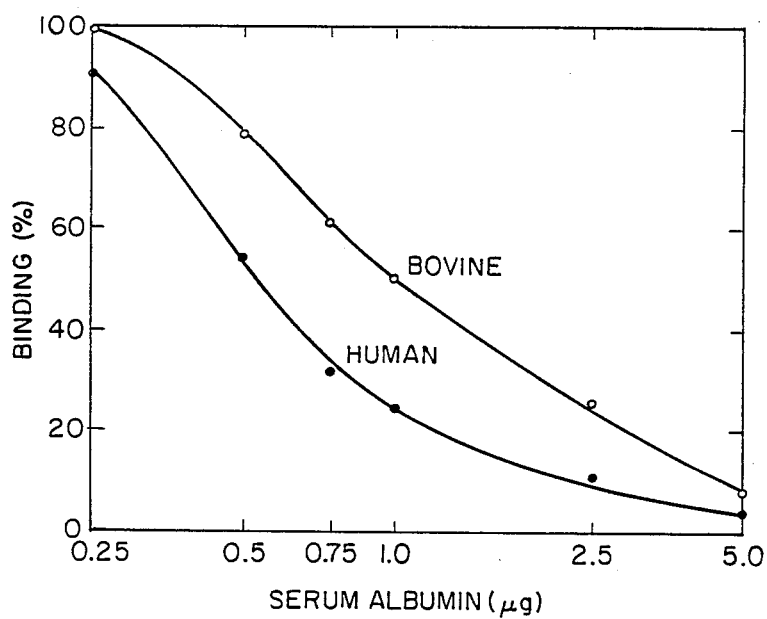
FIG. 5 shows an inhibition curve for a competitive binding assay for simultaneous determination of BSA and HSA, wherein the amount of labeled BSA and HSA is determined by the amplitude of each component of the fluorescence decay curve.

A mixture of dansyl BSA and pyrene butyrate HSA conjugates (100 ul) was incubated with 100 ul of a mixture of anti-BSA (1/75) antibody and anti-HSA antibody (1/125) in the absence of unlabeled BSA and unlabeled HSA, or in the presence of 100 ul of a mixture of varying quantity but fixed ratio of unlabeled BSA and unlabeled HSA (0.25, 0.5, 0.75, 1.0, 2.5, and 5.0 ug of each serum albumin) in PBS buffer containing 0.1% gelatin, 0.1% sodium azide and 1% normal rabbit serum in a total volume of 400 ul at 37° C. for 60 minutes. Thereafter, 100 ul of goat anti-rabbit IgG (20% in PBS) and 100 ul of polyethylene glycol (12.5% in H$_2$O) were added to the reaction mixture and incubated at 37° C. for an additional 30 minutes. The reaction mixture was then centrifuged and the pellet was collected. To the pellet, 200 ul each of 1.0 N NaOH, 0.1 N HCl and PBS were added in sequence to resuspend and stabilize the suspension. Fluorescence was measured with an Horiba time-resolved spectrofluorometer. A two component deconvolution analysis of the fluorescence decay curve of the suspension was performed. The dose response curve was constructed by plotting the concentration of unlabeled BSA or unlabeled HSA against the respective amplitude derived from the deconvolution analysis (FIG. 5).

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A time-resolved fluorescence immunoassay for multiple analytes, comprising the steps of:
a. forming an incubation mixture of:
 (i) antibodies against each analyte;
 (ii) a predetermined amount of fluorescently labeled analytes wherein each fluorescently labeled analyte has a different fluorescene lifetime; and
 (iii) a sample to be tested;
b. incubating the mixture under conditions and for a period of time sufficient for antibody and analytes to complex;
c. determining contemporaneously the amount of each fluorescently labeled analyte bound with antibody as an indication of the amount of each corresponding analyte in the sample, by (i) exciting the fluorescently labeled analyte with a light pulse; and (ii) determining the amplitude of each fluorescence decay curve for the antibody-bound fluorescently labeled analyte by a single amplitude measurement measuring all of the fluorescence reaching the detector from the instant of excitation.

2. A method of claim 1 wherein the antibodies are immobilized on a solid phase.

3. A method of claim 2 wherein the solid phase is separated from the mixture after incubation in Step (c).

4. A method of claim 1, wherein the amplitude of the fluorescence decay curve for each analyte is determined by:
(a) exciting the antibody-bound fluorescently labeled analyte with a single pulse of light energy to induce fluorescence;
(b) separately detecting in a detector and generating:
 (i) an electrical signal corresponding to the fluorescence transient waveform F(t) induced by the single pulse, as distorted by said detector and said pulse, and
 (ii) an electrical signal corresponding to the waveform E(t) of said single pulse, as distorted by the impulse response of said detector,
(c) separately displaying an image of the waveforms F(t) and E(t);
(d) digitizing a predetermined number of data points on each such image, as digital numbers representing points on the waveforms;
(e) storing said numbers in memory as data points of T(t) and F(t); and
(f) calculating the true impulse response fluorescence waveform F(t) from the stored data point numbers by convoluting E(t) with a predetermined trial function F(t)$_{calc}$ having adjustable parameters and comparing the data points of the convoluted F(t)$_{calc}$ with data points corresponding to F(t) data points, wherein the trial function is the sum of a plural number, ith, of exponential curves $A_1\exp(-t/T_2)+A_2\exp(-t/T_2)---A_{ith}\exp(-t/T_{ith})$, where i is the number of analytes, T is the fluorescence lifetime, and the parameter A is proportional to the concentration of each antibody-bound fluorescently labeled analyte.

5. A time-resolved fluorescence immunoassay for multiple analytes, comprising the steps of:
a. providing an immunoadsorbent comprising a solid phase having affixed thereto capture antibodies specific for each analyte to be tested;
b. incubating the immunoadsorbent with a sample to be tested for a period of time and under conditions sufficient for analytes in the sample to complex with the capture antibodies;
c. separating the immunoadsorbent and sample;
d. incubating the immunoadsorbent and a solution containing fluorescently labeled antibodies specific for each analyte, each labeled antibody having a different fluorescence lifetime;
e. separating the immunoadsorbent and the solution;
f. determining contemporaneously the amount of each conjugate associated with the immunoadsorbent as an indication of the amount of each analyte in the sample by (i) exciting the fluorescently labeled antibodies with a light pulse; and (ii) determining the amplitude of the fluorescence decay curve of each conjugate by measuring all of the fluorescence reaching the detector from the instant of excitation with a single amplitude measurement.

6. An assay of claim 5, wherein the solid phase is a bead, microwell, or test tube.

7. A method of claim 5, wherein, the amplitude is determined by:
(a) exciting the fluorophores associated with the immunoadsorbent with a single pulse of light energy to induce fluorescence;
(b) separately detecting in a detector and generating:
 (i) an electrical signal corresponding to the fluorescence transient waveform F(t) induced by said single pulse, as distorted by said detector and said pulse, and
 (ii) an electrical signal corresponding to the waveform E(t) of said single pulse, as distorted by the impulse response of said detector,
(c) separately displaying an image of said waveforms F(t) and E(t);

(d) digitizing a predetermined number of data points on each such image, as digital numbers representing points on said waveforms;

(e) storing said numbers in memory as data points of T(t) and F(t); and (f) calculating the true impulse response fluorescence waveform F(t) from the stored data point numbers by convoluting E(t) with a predetermined trial function F(t)$_{calc}$ having adjustable parameters and comparing the data points of the convoluted F(t)$_{calc}$ with data points corresponding to F(t) data points, wherein the trial function is the sum of a plural number, ith, of exponential curves $A_1\exp(-t/T_2)+A_2\exp(-t/TH2Y) \text{---} A_{ith}\exp(-t/T_{ith})$, where i is the number of analytes, T is the fluorescence lifetime, and the parameter A is proportional to the concentration of each antibody-bound fluorescently labeled analyte.

8. A time-resolved fluorescence immunoassay for multiple analytes, comprising the steps of:

a. providing an immunoadsorbent comprising a solid phase having affixed thereto capture antibodies specific for each analyte to be tested;

b. incubating the immunoadsorbent with a sample to be tested for a period of time and under conditions sufficient for analytes in the sample to complex with the capture antibodies;

c. separating the immunoadsorbent and the sample;

d. incubating the immunoadsorbent with a solution containing second antibodies against each of the analytes, the incubation being carried out under conditions and for a period of time which permits the second antibodies to complex with analyte bound to the immunoadsorbent wherein each of the second antibodies are antigenically distinct;

e. separating the immunoadsorbent and the solution;

f. incubating the immunoadsorbent and a solution containing fluorescent antibody conjugates against the second antibodies, the conjugates comprising an antibody against each second antibody labeled with a fluorophore, each conjugate having a different fluorescence lifetime;

g. separating the immunoadsorbent and the solution; and h. determining contemporaneously the amount of each conjugate associated with the immunoadsorbent as an indication of the amount of each corresponding analyte in the sample by (i) exciting the fluorophone with a light pulse; and (ii) determining the amplitude of the fluorescence decay curve of each fluorophore by measuring all of the fluorescence reaching the detector from the instant of excitation with a single amplitude measurement.

9. A method of claim 8, wherein the solid phase is a bead, microwell or test tube.

10. A method of claim 8, wherein the capture antibodies are monoclonal antibodies, the second antibodies are polyclonal antibodies, and the conjugates comprise fluorescently labeled polyclonal antibodies.

11. A method of claim 8, wherein the conjugates have fluorescent lifetimes which differ from each other by greater than about 20 nanosec.

12. A method of claim 8 wherein the amplitude is determined by:

(a) exciting fluorescently labeled antibody associated with the immunoadsorbent with a single pulse of light energy to induce fluorescence;

(b) separately detecting in a detector and generating:

(i) an electrical signal corresponding to the fluorescence transient waveform F(t) induced by said single pulse, as distorted by said detector and said pulse, and (ii) an electrical signal corresponding to the waveform E(t) of said single pulse, as distorted by the impulse response of said detector, (c) separately displaying an image of said waveforms F(t) and E(t);

(d) digitizing a predetermined number of data points on each such image, as digital numbers representing points on said waveforms;

(e) storing said numbers in memory as data points of T(t) and F(t); and (f) calculating the true impulse response fluorescence waveform F(t) from the stored data point numbers by convoluting E(t) with a predetermined trial function F(t)$_{calc}$ having adjustable parameters and comparing the data points of the convoluted F(t)$_{calc}$ with data points corresponding to F(t) data points, wherein the trail function is the sum of a plural number, ith, of exponential curves $A_1\exp(-t/Tphd\ 2)+A_2\exp(-t/TH2Y) \text{---} A_{ith}\exp(-t/T_{ith})$, where i is the number of analytes, T is the fluorescence lifetime, and the parameter A is proportional to the concentration of each antibody-bound fluorescently labeled analyte.

* * * * *